United States Patent
Scharf

[11] 3,975,644
[45] Aug. 17, 1976

[54] FLAW DETECTING METHOD AND APPARATUS

[76] Inventor: Erich Scharf, 20 Atwater Place, Massapequa, N.Y. 11758

[22] Filed: Aug. 16, 1974

[21] Appl. No.: 498,231

[52] U.S. Cl. .............................. 250/563; 250/227; 250/572; 356/200
[51] Int. Cl.² ..................................... G01N 21/32
[58] Field of Search .......... 250/562, 563, 559, 548, 250/572, 227; 356/200, 237, 238

[56] References Cited
UNITED STATES PATENTS

| | | | |
|---|---|---|---|
| 3,257,563 | 6/1966 | Laurent | 250/563 |
| 3,427,462 | 2/1969 | Cist | 250/562 |
| 3,531,650 | 9/1970 | Cronin | 250/237 G X |
| 3,566,083 | 2/1971 | McMillin | 250/227 X |
| 3,797,943 | 3/1974 | Nagao et al. | 356/200 |
| 3,885,131 | 5/1975 | Franceschini et al. | 250/570 X |

*Primary Examiner*—Eugene La Roche
*Attorney, Agent, or Firm*—Steinberg and Blake

[57] ABSTRACT

A material monitoring apparatus and method for determining the quality of a sheet of material by detecting dirt particles, flaws in the contents of the material or the composition of the material. The apparatus includes a housing held by a support and positioned above the sheet of material being monitored. A plurality of photoelectric sensing devices are located within the housing. A series of apertures of progressively different sizes are located one behind the other in the longitudinal direction on the bottom of the housing facing the sheet of material. Each of the photoelectric sensing devices are positioned to receive light entering through a respective one of the apertures, wherein the amount of light received is dependent upon the quality of the sheet material being monitored. The light received by the photoelectric sensing devices are converted into electrical signals by means of electronic control circuitry. These electrical signals are then appropriately used to indicate the quality of the material being monitored.

13 Claims, 9 Drawing Figures

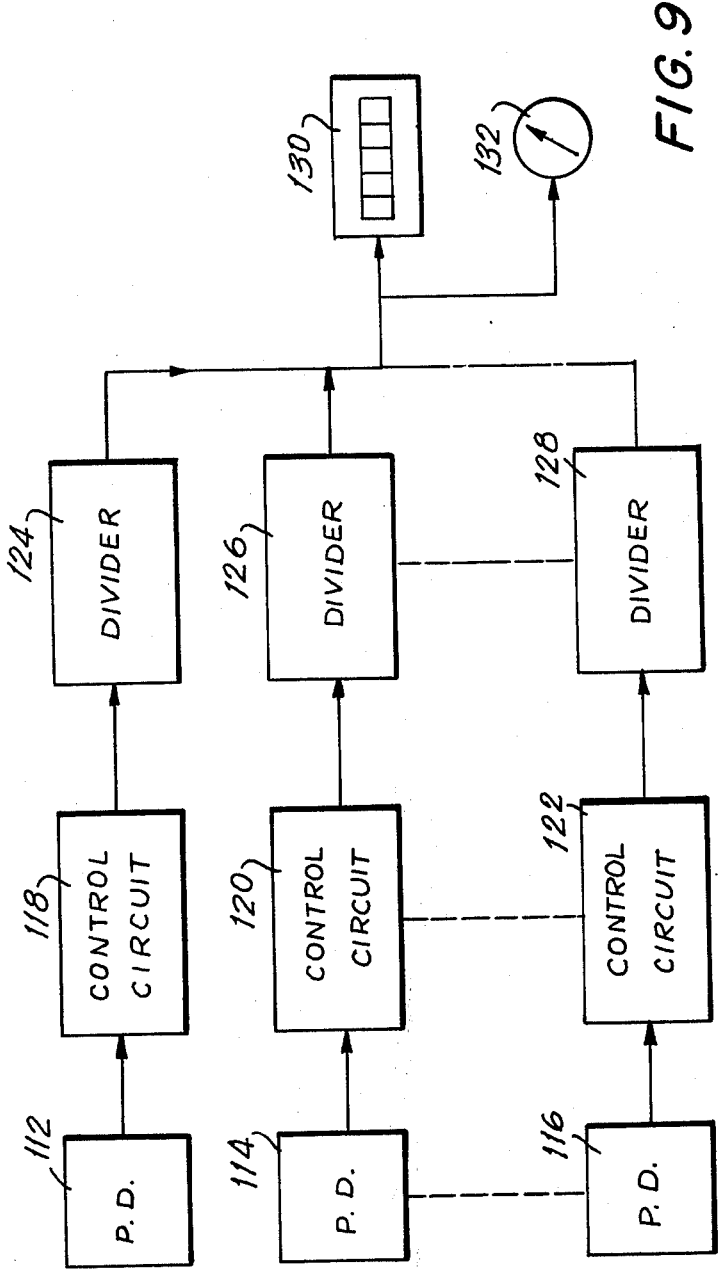
FIG. 8
FIG. 6
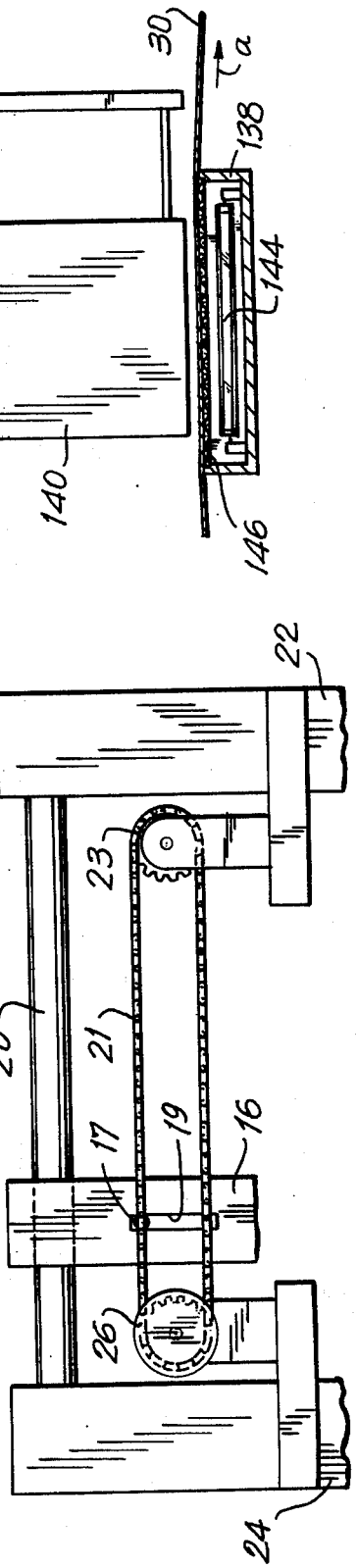
FIG. 9

FLAW DETECTING METHOD AND APPARATUS

BACKGROUND OF THE INVENTION

The present invention relates to quality control.

In particular, the present invention relates to material monitoring apparatus for determining the quality of a sheet material being manufactured.

In various manufacturing industries, such as in the manufacture of paper and paperboard, there is a need for determining the quality of the material being produced. Thus, in the manufacture of paper there is generally a need to know the dirt content of a running web, as well as the number of flaws and the fiber distribution in the web. The monitoring of the paper quality not only determines the value of the finished paper material, but also provides an indication of the effectiveness of the manufacturing equipment and the filtering system being used, as well as providing an indication of the quality of the original stock material. At the present time, quality control of the manufactured paper is generally accomplished using off-line, laboratory methods. Samples of the finished product are selected and using laboratory equipment, the amount of dirt content as well as other defects are measured and catalogued.

While such off-line laboratory methods may provide accurate results, the time required for completing analysis is often excessive and provides too great a delay for immediate corrective action. For example, by the time a particular sample of paper is checked for its quality, that batch of paper will have been passed from the machine, and may very well be already packed for shipment to a distributor. Thus, it will often be too late to remove the batch of paper and use it for other purposes. Furthermore, should a particular batch of paper indicate that the original stock is of a poor quality, it would be advisable to change the original stock. However, the excessive delay resulting from the effective testing may make it too late to change the stock and the poor quality stock will be used up before there is any chance to change it. Additionally, the problem causing a poor quality paper may result from poor filtering operation within the manufacturing process. This might easily be corrected if the problem could be detected within s reasonable time. Accordingly, it would be beneficial to provide on-line monitoring of the material to provide an indication of the quality of the paper being produced during the course of the manufacturing process.

SUMMARY OF THE INVENTION

It is accordingly a primary object of the present invention to provide apparatus for on-line monitoring of the quality of material during the manufacture thereof.

In particular, it is an object of the present invention to provide apparatus which can determine the dirt content in material being manufactured, and specifically to quantize the size of the dirt particles detected in the material.

It is especially an object of the present invention to provide an apparatus which can monitor the dirt content of a running web of material during manufacture.

Also, it is an object of the present invention to provide an apparatus which can monitor the fiber distribution in a finished sheet of manufactured material such as paper.

It is a particular object of the present invention to provide a photoelectric web inspection system which is usable in on-line equipment.

It is also an object of the present invention to provide a method for monitoring the quality of a material being manufactured, and for determining the presence and extent of foreign particles therein, as well as defects and other flaws which may be present in the material.

According to the invention the material monitoring apparatus includes a housing means held by a support means which positions the housing means above the running sheet of material being monitored. A drive means moves the housing means in a transverse direction across the sheet of material. A plurality of photoelectric sensing means are located within the housing means. A series of apertures, located one behind the other in the longitudinal or sheet-moving direction, are provided at the bottom of the housing means facing the sheet of material, the apertures having progressively different sizes. Each photoelectric sensing means is positioned to receive light entering through one of the apertures, wherein the amount of light received is dependent upon the quality of the sheet material. Electronic control circuitry coupled to the photoelectric sensing means converts the light received into electrical signals, and a display means, responsive to the electrical signals, provides an output indication of the quality of the material being monitored.

Also, a method of the present invention is provided for determining the quality of a sheet of material being manufactured. The method includes, directing light onto or through the travelling sheet material being monitored, and detecting through a series of apertures the amount of light travelling from the surface of the sheet. The apertures are located one behind the other in the direction of sheet movement, and the apertures have progressively different sizes. The amount of detected light is then converted into electrical signals, wherein the electrical signals are dependent upon the quality of the sheet of material being monitored. The electrical signals are then used to indicate the quality of material. The apertures may be continuously moved in a transverse direction across the travelling material, while the detecting, converting and indicating steps are carried out.

BRIEF DESCRIPTION OF DRAWINGS

The invention is illustrated by way of example in the accompanying drawings which form part of this application and in which:

FIG. 6 is a fragmentary transverse view, taken along line 6—6 of FIG. 1 in the direction of the arrows, show

FIG. 8 is a schematic illustration of another type of electronic circuitry which may be used with the invention; and FIG. 9 is a fragmentary schematic partly sectional illustration of another embodiment of a monitoring apparatus and method according to the invention.

DESCRIPTION OF PREFERRED EMBODIMENTS

Figure 1:
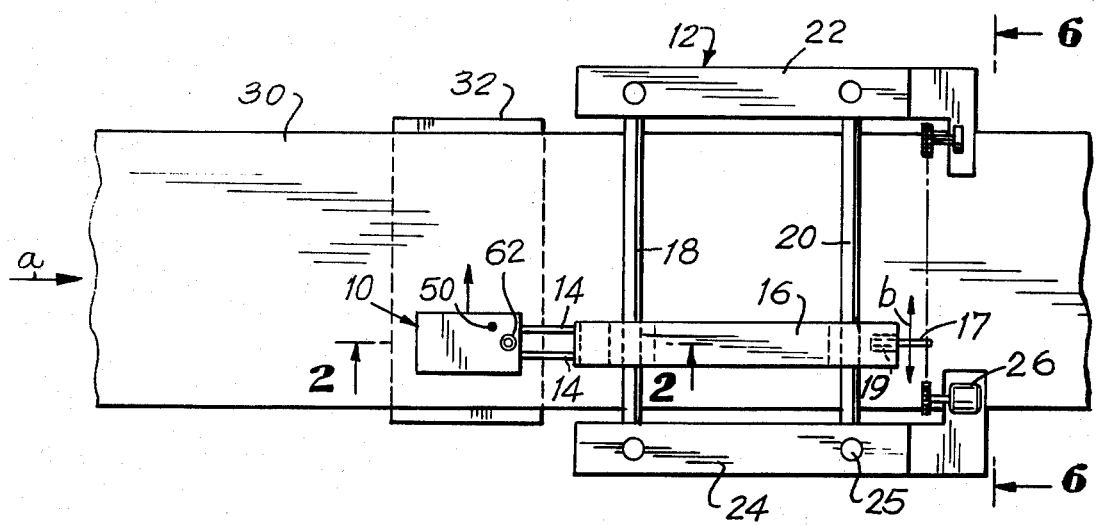
FIG. 1 is a plan view of one embodiment of a monitoring apparatus of the present invention.

Referring now to FIGS. 1 through 6, wherein like parts are identified by like reference characters, there is shown a housing means 10 coupled to a carrier structure, shown generally at 12, by means of leaf springs 14. Four parallel springs are shown connected two at the top and two at the bottom of the housing 10 to thereby cantilever the housing 10 from an L-shaped supporting arm 16, which forms a movable assembly with housing 10 and springs 14. The supporting arm 16 is formed with bores slidably receiving bars 18, 20 coupled between upright side members 22, 24 secured to a base (not shown) by posts 25. A drive motor 26 continuously drives the arm 16 back and forth in the directions b, along the bars 18, 20 away from support member 22 toward the support member 24 then in the opposite direction back toward member 22, and so on. This movement can be achieved by a structure as shown in FIG. 6. Thus, the supports 22 and 24 have extensions one of which carries the motor 26 which serves to drive a sprocket wheel by means of which an endless sprocket chain 21 is driven, this chain being guided around a second wheel 23 supported for rotary movement by the extension of the support 22. The endless sprocket chain 21 carries a pin 17 which is received in a slot or groove 19 formed in the support arm 16 and extending vertically in the manner illustrated in FIG. 6. As is apparent from FIG. 1, the drive pin 17 extends from the endless sprocket chain 21 to the left into the groove or slot 19. Thus, as the chain 21 is continuously driven the pin 17 will act on the arm 16 to move it first in one direction and then in the opposite direction along the bars 18 and 20.

The housing means 10 is positioned slightly above the sheet material 30 over which it passes. During the manufacture or other treatment of the sheet material, the material is typically passed from roller to roller during processing. At the location of the monitor housing 10 a guide means or supporting block 32 is positioned beneath the sheet material to provide a support for the web as it is monitored. The web therefore moves in a longitudinal direction, as shown by the arrow a, while the housing moves in a transverse direction b, across the web.

Figure 2:
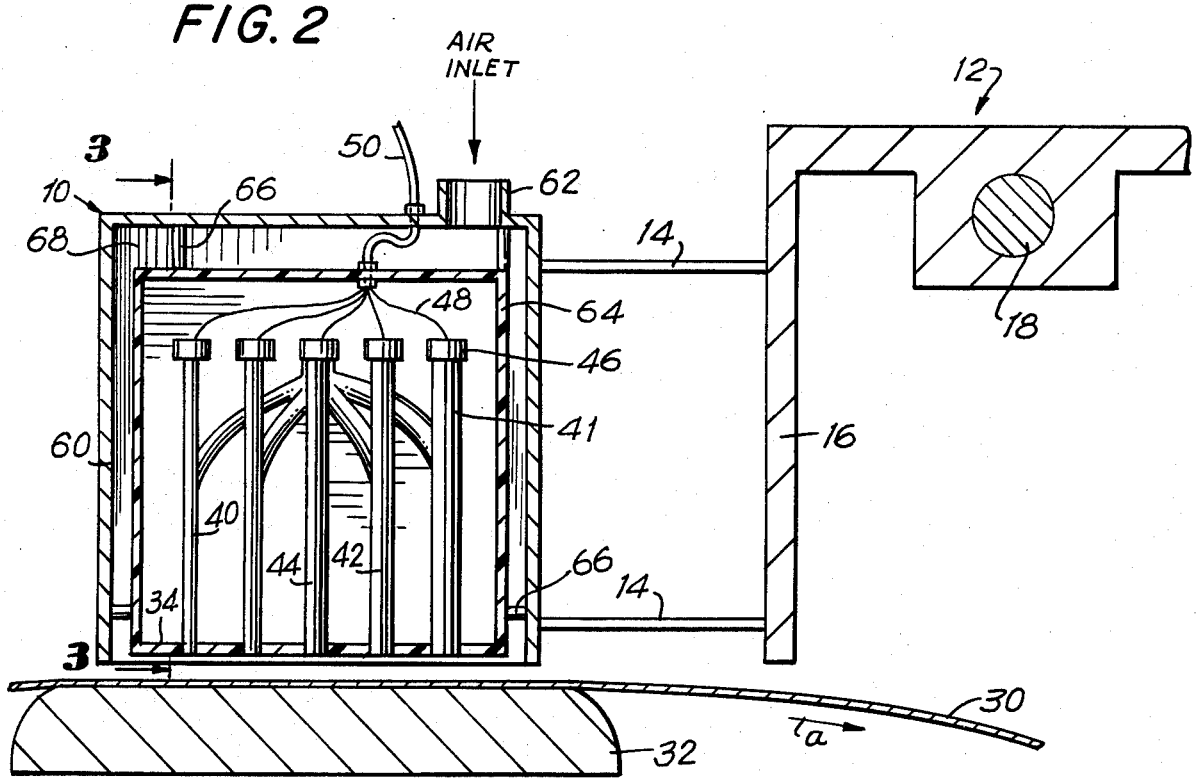
FIG. 2 is a fragmentary sectional longitudinal elevational view of the apparatus of FIG. 1 taken along line 2—2 of FIG. 1 in the direction of the arrows.
Figure 5:
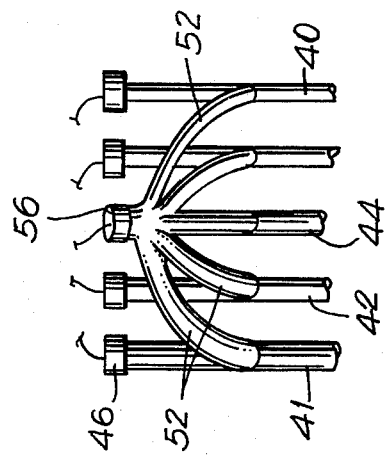
FIG. 5 is a fragmentary elevation of the fiber optics, taken along line 5—5 of FIG. 3 in the direction of the arrows, and indicating how the illumination for all of the fiber optics comes from a single light source.
Figure 4:
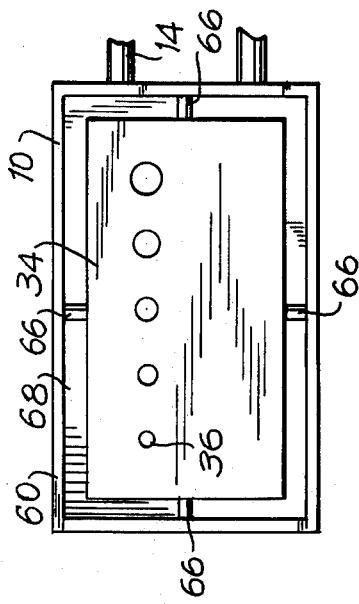
FIG. 4 is a view of the housing and its interior as seen when looking upwardly from the sheet in FIGS. 1 and 2.

The housing 10 is open at its bottom and houses a hollow enclosure 64 having a bottom wall 34 formed with a plurality of apertures 36 of different sizes (FIG. 4). The apertures 36 are located one behind the other in a longitudinal direction and face the running web. As shown in FIG. 4, the apertures are of progressively larger sizes. Additionally, the apertures could have varying shapes including circular shapes, elliptical shapes, etc. A series of fiber optics 40, 41, 42, 44, . . . are shown interconnecting the apertures with electronic photodetector devices 46, each of which is positioned at the opposite end of the fiber optic. As shown in FIG. 2, each of the fiber optics are of a different thickness, such that a thinner fiber optic is coupled to a smaller aperture, and progressively thicker fiber optics are coupled to the progressively larger apertures. However, a single sized fiber optic could also be used wherein the fiber is thick enough to fit the largest aperture. A feature of the invention is that the apertures are of different sizes to permit differently sized areas of the web to be viewed. The photoelectric detectors 46 are electrically connected by means of wires 48 to a cable 50 extending out of the housing 10.

Figure 3:
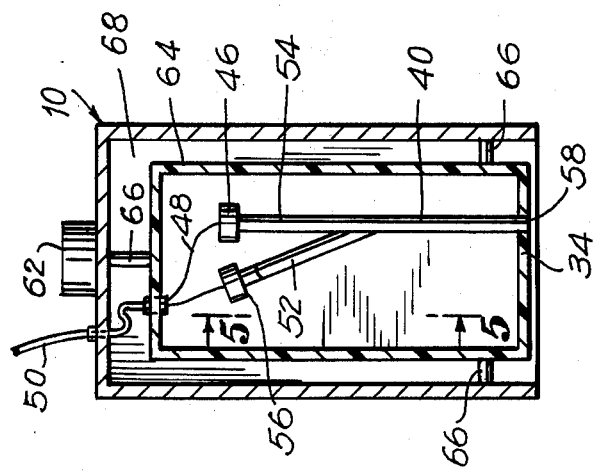
FIG. 3 is a sectional transverse view of the apparatus of FIGS. 1 and 2 taken along line 3—3 of FIG. 2 in the direction of the arrows.

In one embodiment of the invention, as shown in FIG. 3, the fiber optic is a retroreflective fiber optic assembly. The fiber optic 40 has two paths, namely a first path including branch 52 and a second path including branch 54. Light from a light source 56, which is common to all of the branches 52 (FIG. 5), enters through the input of the branch 52 and is transmitted along branch 52 to the sensing end 58 of fiber optic 40 wherein the light is emitted from the fiber optic. The light will then reflect from the surface of the material being monitored and will again be detected by the fiber optic 40. The reflected light will now pass through branch 54 to the output end where it is coupled to the photoelectric detector 46. The several fiber optics are of the same construction except that they have different sizes, corresponding to the differently sized apertures as shown in FIG. 2, with all of the fiber optics receiving light from the common light source through the series of branches 52 as described above, and each fiber optic transmits the light at its output end to a photoelectric detector 46, as shown most clearly in FIGS. 2 and 5.

The housing means 10 is shown including an outer casing 60 having a nozzle 52 extending from the upper surface thereof. Within its outer casing 60, the housing means 10 carries the inner container 64 supported by means of rods of screws 66 to define air chamber 68 between the outer casing 60 and the inner container 64. The photoelectric assemblies are contained within the inner container 64 and the apertures 36 are formed on the bottom 34 of the inner container 64. The bottom of the outer casing 60 is open. Air is fed into the housing through the nozzle 62, passes into the air chamber 68 and is emitted from the bottom of the outer casing. The air therefore passes along the surface of the sheet of material being monitored. The air provides a layer of air such that the housing 10 rides along an air bearing and is supported adjacent to but in spaced relationship with the surface of the sheet material being monitored.

The operation of the apparatus will now be explained in connection with the manufacture of a paper product by way of example. The web being manufactured generally exhibits some degree of nonuniformity. Such nonuniformity can result from the presence of particles, such as dirt in the surface of the material. When a light is directed onto the surface of the web, the amount of light reflecting from the surface varies in accordance with the composition of the material. Thus, less light will reflect from a black dirt particle than from the normal surface of the paper. When viewed optically, the amount of light received will be nonuniform. To some extent minor nonuniformities will exist due to the normal variation of composition of the paper. However, large differences in reflectivity will be present when a dirt particle of a given size or larger is detected in the surface of the material. The present apparatus therefore provides the means for determining the presence of such dirt particles and furthermore permits quantizing the dirt particles to determine the size and extent of such flaws in the paper surface.

Light is directed through the retroreflective fiber optic assembly onto the surface of the web. The light reflects from the surface and is received by the retroreflective fiber optic assembly. The amount of light reflected is then detected by the photodetector located at the output of the fiber optic assembly.

Each of the photodetectors has an electronic circuit connected to it, which converts the amount of light detected into an electrical signal. The electrical signal will be a substantially continuous one representing the continuous amount of light normally received from a normal consistency in the paper surface. However, when a spot, such as a black spot, is present in the paper, the amount of light reflected will suddenly decrease. This decrease will cause a sudden change in the amount of light detected by the photodetector, and accordingly will result in a sudden change in the electrical signal. These changes can then be converted to pulses which are counted. The count will represent the number of the black spots which a particular photodetector sees as the housing moves transversely across the travelling web.

The electrical circuitry associated with each of the detectors can include a biasing circuit, such as a threshold detector, whereby only a change of a sufficient magnitude will be connected to an output pulse to be counted. Thus, it is possible that a small particle of dirt is present in the surface which only partially covers the aperture and therefore, only blocks a portion of the reflected light. Although a slight change in the output signal will occur, the magnitude of the change will not be sufficient to produce an output pulse. On the other hand, when a large particle of dirt is present which covers the entire aperture, a pulse will be produced. By setting the threshold detector at a certain level, it is possible to bias the electrical circuitry such that a pulse will be produced only in response to particles larger than a given size.

Additionally, each of the apertures are of different sizes, as for example, progressively larger sizes. Thus, by way of example, six apertures could be utilized with the respective sizes being 0.4mm, 0.8mm, 1.6mm, 3.2mm, 6.4mm, and 12.8mm. This system provides an increase in size by a factor of 2 from one aperture size to the other aperture size and accordingly would provide an exponential type of scale. By appropriately biasing each of the electrical circuits connected to the respective apertures, it is possible to obtain a system whereby a particle of a given size would produce an output signal from certain of the photoelectric detectors but will not produce an output from other photoelectric detectors. For example, given the above described set of aperture sizes, a particle having a size of approximately 1.0mm would completely cover the smallest two apertures and would therefore produce a large change in output electrical signal which would be registered as an output from each of those apertures. However, when viewed under the third aperture, having a size of 1.6mm, only a portion of that aperture would be covered. Thus, while there would be a slight change in the output signal, by setting the threshold detector associated with that aperture at a particular point whereby a large change in output signal is needed, the slight change resulting from this particle of dirt would be insufficient to produce an output count from the third aperture. Thus, depending upon which electrical detector produces an output, it is possible to determine the minimum effective size of the particle of dirt which has been detected. The "effective" size is equal to the optical contrast multiplied by the area or size of the particle. Thus, assuming that the sheet material which is being monitored has a predetermined basic color, the detection is determined not only in accordance with the size of the particle but also in accordance with the contrast with the basic color. For example if the sheet is white, a solid black speck will have a greater degree of contrast than a grey speck. Therefore the same amount of light will be received from a grey speck which is larger than a deep black speck, so that what is detected is the "effective" size which is a combination of the contrast and actual size of a given particle of dirt or other material which constitutes a flaw.

The electronics associated with each of the photoelectric detectors can be assembled from components well known in the art, and various types of detecting circuits can be utilized. One such detecting circuit is shown by way of example in FIG. 7. The steady state output of photodetector 46 is shown as being a generally constant signal with a slight amount of noise depending upon the variations of the content of the surface of the web. However, at the occurrence of a dirt spot which effectively covers the aperture, a large reduction in the output signal will occur, as for example shown at points 82, 84. The output signal from the photodetector is amplified and inverted in amplifier 86 to produce the signal shown at the output thereof. The amplified signal then passes through a threshold detector 88, which produces signal outputs in response to the sudden reductions 82, 84. These signals are shown at 90 and 92. By setting the threshold detector at a particular desired biasing value, the signals which result from a partial covering of the aperture due to a relatively small particle size are eliminated. Only when a large enough particle is viewed in a particular aperture will the threshold detector produce a signal. The output from the threshold detector 88 is differentiated by differentiator 94 which produces spike pulses 96, 98 to trigger a trigger circuit 100, such as a Schmitt trigger or other type of multivibrator, thereby producing a fixed time duration output pulse 102, 104 corresponding to each of the larger size particles detected by the photodetector 46. The pulses can then be counted on counter 106 wherein the total count represents the total number of particles of sufficient size detected by that particular photodetector through its corresponding aperture. Alternately, or simultaneously, the signals can be integrated in integrator 108 and read on meter 110 whereby the meter 110 provides a reading of the number of spots per given length of sheet material.

Figure 7:
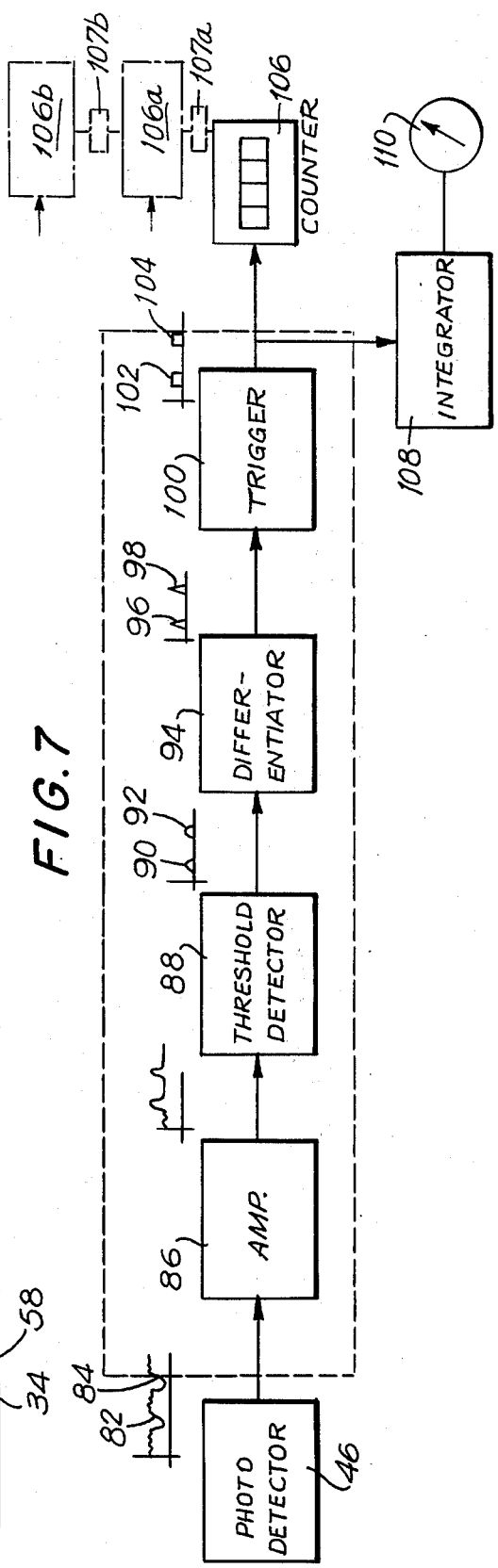
- FIG. 7 is a schematic diagram of one possible type of electronic circuitry which may be used with the invention.

Each of the apertures has its own individual circuitry of the type shown in FIG. 7, and each aperture has its own output counter. In this manner, utilizing 6 apertures, 6 individual counters could be provided and the count on each counter indicates the number of particles of a given size contained within the sampling area of the particular web. It is noted, that since the paper will generally be moving in a longitudinal direction and the housing containing the apertures and photodetectors would be moving in a transverse direction, the sampling line would effectively be a wave such as a sine wave across the running web. However, this sampling would be sufficient and, in fact, would provide a better analysis than is presently available using off-line, laboratory methods.

Of course, it is to be understood that the speed with which the detecting structure of the invention traverses the traveling sheet is relatively slow or only a small fraction of the speed of longitudinal travel of the sheet. Thus, for example, the sheet which is being monitored will customarily travel on the order of 1,000 feet per minute, while the housing 10 will be traversed by the structure shown in FIG. 6, for example, through a complete traversing cycle from a given starting point back and forth, back to the starting point, in a time of 2–5 minutes. This relationship is such that the housing 10 may be considered as being practically stationary with respect to the travelling sheet at any given instant, and in fact it is within the scope of the present invention to provide a construction where the traversing structure of FIG. 6 is omitted and the housing 10 with the structure carried thereby remains stationary at a part of the sheet so that only a linear detection is made, with an average reading being achieved which perhaps is not as precise as the average reading achieved by utilizing the traversing method and structure of FIG. 6. Thus, no attempt is made to "see" the entire area of the sheet, but rather an attempt is made to detect a sample which is large enough to give an accurate indication of the quality of the sheet. As a result, a flaw which covers the smallest aperture in its entirety may also be large enough to cover the next larger aperture in its entirety, and so on. Assuming that the flaw is large enough to fully cover the smallest aperture and the next larger aperture, but is not large enough to give a signal at the third aperture, then of course a superfluous reading would be given at the smallest aperture. For this reason it is preferred to interconnect the several counters in the manner shown schematically in FIG. 7. Referring to the right of FIG. 7, there are schematically shown additional counters 106a, 106b, etc., which receive the outputs from the trigger circuits 100 of the additional electronic circuit units which are connected to the additional photodetectors 46 which are carried by the successively larger fiber optics. Assuming that the electronic circuitry shown in FIG. 7 is connected to the smallest fiber optic and that the counter 106a is connected to the next larger fiber optic, while the counter 106b is connected to the third fiber optic, then if the counter 106a is actuated immediately after the counter 106 is actuated, through the unit 107a which interconnects the counter 106 with the unit 106a, as soon as the counter 106a is triggered the counter 106 is operated from the unit 107a in response to operation of the counter 106a in a reverse direction so as to subtract a count. Therefore, when the flaw is large enough to completely cover the smallest aperture the count initially transmitted to the counter 106 is added thereto but then is immediately subtracted therefrom when the same flaw causes the counter 106a to be triggered, and if this same flaw is large enough to provide through the third aperture a triggering of the third counter 106b, the count added at the counter 106a will automatically be subtracted therefrom by the unit 107b which responds to the actuation of the counter 106b from the fiber optic connected to the third aperture. The units 107a, 107b, etc. for interconnecting a series of counters for subtracting from one counter what has previously been countered thereby when the next counter is actuated are well known. For example such units may be purchased from National Semiconductor Corporation which shows in its June 1973 catalog, at page 1–99 a digital integrated circuit suitable for this purpose. Through such an arrangement the "effective" size of a flaw will be accurately determined.

Of course, after a given length of sheet material has travelled past the sensing structure of the invention, whether it remains stationary or traverses the travelling sheet material, the entire structure is zeroed and a new operating cycle is started. For example after each 5,000 feet of sheet travel or after each 10,000 feet of sheet travel, which may be detected through known structures, the entire sensing structure will be automatically zeroed and a new operating cycle will start, and through suitable recorders connected to the counters or the integrator units 108, 110 it is possible to record the quality of the sheet material. These recordings may be printed or marked through suitable recording pens on automatic printout sheets which are constantly consulted by the operator to check on the quality of the sheet material.

Furthermore, it is possible to connect a digiswitch to the sensing structure for detecting when the flaws are greatly beyond the acceptable limit. Such digiswitches are well known. They may be obtained, for example, from B.F. Enterprises of Redding, Mass., which shows in their catalog 7310, at page D, a rotary thumbwheel switch suitable for this purpose. Thus, where the counter triggered from the sensing structure connected to the largest aperture repeatedly counts a relatively large number in an extremely short time, the integrator unit 108, 110 or even the counter associated with the largest aperture may be set to actuate the digiswitch automatically when reaching a given count so as to automatically close the circuit of an alarm, such as a horn, for example, thus giving a warning to the operator who will immediately take corrective action when such an indication is given since under these circumstances something radically wrong has occurred.

Therefore, with the method and apparatus of the invention a sampling is taken of the sheet material with an indication being given of the frequency of occurrence of flaws, and it is possible to consult the apparatus of the invention in order to determine whether these flaws are maintained within acceptable limits. In this way it is possible to designate that the sheet material is of a given quality or it is possible to take corrective measures to improve the quality without interrupting the operation of the machine.

Instead of utilizing individual counters for each aperture, it is possible to have a system as shown in FIG. 8 utilizing a single counter to provide an indication of the total quality of the paper. Thus, the photodetectors 112, 114 . . . 116, corresponding to detectors 46, are connected respectively to control circuits 118, 120 . . . 122. The individual control circuits typically correspond to that portion shown within the dotted outline of FIG. 7. At the output of each of the control circuits is a circuit providing a weighting function to each of the output counts. Thus, a count of 1 from the smallest aperture indicates a small particle size. A count of 1 from the largest aperture indicates a very large particle size. It is therefore possible to have 5 counts from the smallest aperture before the counter will increase its value by one, while a single count from the highest aperture automatically increases the value of the counter by 1. This weighting function can be achieved by the use of dividers 124, 126 . . . 128 whereby each of the counts from the respective apertures is divided down in accordance with the desired weighting function. The total output from each of the dividers then passes through a single counter 130 and/or meter 132. The counter and/or meter therefore provides a single output from all of the apertures and this output value represents the total quality of the paper.

Other types of readout analysis could be performed by well known electronic techniques. The output could be related to the footage of web being monitored as counts per unit length or to other similar parameters.

In addition to providing an indication of the dirt content, the apparatus of the present invention could be used in the monitoring of the formation of the paper material, i.e. the fiber distribution in the finished paper sheet. For this embodiment, rather than utilizing a retroreflective system, a back lighted system can be utilized as is shown in FIG. 9. Thus, the hollow support member 138 has in its interior a lamp 144 connected to any source of current and situated beneath a light diffusing plate 146 from which diffused light travels through the web 30 travelling in the direction a. The transmitted light is picked up by the apparatus 140 which includes the series of apertures and corresponding fiber optics. Thus, each fiber optics in this case has a single path which receives the light transmitted through the web being monitored. The light detected by the photodetector at the end of the fiber optics produces a signal which varies in accordance with the fiber content of the paper. This signal is mathematically processed, as for example by a Fourier analysis processor, to produce an output signal which can then be displayed to show a visual indication of the fiber distribution. The signal could be further processed to provide a composite signal descriptive of the particular material under inspection.

The apparatus of the present invention could also provide a general photoelectric web inspection system. Here the usual technique is to observe the web through a fixed aperture system. However, this can lead to a situation where the system will either see too much of the web or depending on the magnitude of the defect to be detected and the variability of the web will not see enough of the web. Such a standard system can be replaced by the multiple aperture system, as described hereinabove, which can provide the required flexibility of operation to make the system more effective.

It is well known that certain aperture shapes favor the detection of certain classes of defects. For example, small scratches are best detected by means of a circular viewing field. In order to determine specific types of flaws, the different sized apertures in the present invention could each have varying shapes to thereby detect specific types of flaws desired.

What is claimed is:

1. In a material monitoring apparatus for determining the quality of a sheet material, an assembly including housing means and support means connected with said housing means for supporting the same closely adjacent to a surface of a travelling sheet of material without any optical structure between said housing means and said sheet, said housing means being formed with a series of apertures which are arranged in a row extending in the direction of sheet travel with said apertures being of progressively larger sizes in the direction of sheet travel and being directed toward the sheet, a plurality of photoelectric sensing means carried by said housing means for receiving light respectively entering through said apertures thereof directly from the sheet while travelling only through a relatively small air gap between the sheet and the housing means closely adjacent thereto, the amount of light received being dependent upon the quality of the sheet material, traversing means operatively connected with said assembly for moving the latter cyclically first in one direction and then in an opposite direction transversely across the sheet while the latter travels longitudinally, electronic circuit means electrically connected with said plurality of sensing means for converting the light received thereby into electrical signals, and indicating means electrically connected with said electronic circuit means for responding to the electrical signals for indicating the quality of the material.

2. The combination of claim 1 and wherein each of said photoelectric sensing means includes a retroreflective fiber optical structure having an input end, and output end, and a sensing end, said structure receiving light at said input end and transmitting the light to said sensing end to be directed therefrom to and reflected back from the sheet, said sensing end receiving the reflected light and transmitting it to said output end.

3. The combination of claim 1 and further comprising spring means interconnecting in cantilever fashion said housing means and said support means.

4. The combination of claim 1 and wherein said circuit means includes threshold detection means associated with each of said photoelectric sensing means and wherein each of said threshold detection means is set at an effectively higher threshold value corresponding to the progressively larger sized apertures such that a larger sized flaw is required in order to produce an electrical signal from the photoelectric sensing means associated with a larger sized aperture.

5. The combination of claim 1 and further comprising illuminating means located on the side of the sheet material opposite to the side where said housing is positioned, whereby said photoelectric sensing means senses the light transmitted through the sheet material.

6. The combination of claim 1 and further comprising sheet guide means for guiding the sheet material to travel along a path adjacent said housing means.

7. The combination of claim 1 and wherein said circuit means includes weighting circuitry to weigh appropriately the output of each electrical signal in accordance with the size of the corresponding aperture.

8. The combination of claim 1 and wherein each of said photoelectric sensing means comprises means for receiving light travelling from the sheet through an aperture and photodetector means positioned for receiving the light.

9. The combination of claim 8 and wherein said electronic circuit means includes amplifier means receiving an output signal from said photodetector means, threshold detection means for receiving the amplified output signal and for producing individual signals corresponding to values of the amplified output signal which are greater than the threshold, means receiving the individual signals from said threshold detection means and producing fixed trigger pulses corresponding to each individual signal, and trigger means receiving said trigger pulses and for producing a pulse of fixed duration in response to each such trigger pulse.

10. The combination of claim 9 and wherein said indicating means includes digital counter means receiving said fixed duration pulses for counting them.

11. In a material monitoring apparatus for determining the quality of a sheet material, an assembly including housing means and support means connected with said housing means for supporting the same adjacent a surface of a travelling sheet of material, said housing means being formed with a series of apertures directed toward the sheet and respectively having different sizes, a plurality of photoelectric sensing means carried by said housing means for receiving light respectively entering through said apertures thereof, the amount of light received being dependent upon the quality of the sheet material, electronic circuit means electrically connected with said plurality of sensing means for converting the light received thereby into electrical signals, indicating means electrically connected with said electronic circuit means for responding to the electrical signals for indicating the quality of the material, and an air-bearing means operatively connected with the said assembly for supporting the latter on air over the travelling sheet, said housing means including an outer casing having an open end adjacent said sheet material and an inner container supported within said outer casing and defining an air chamber therewith, said photoelectric sensing means being situated within said inner container, and nozzle means coupled to said air chamber for directing air from said nozzle means through said air chamber to escape from the bottom of said outer casing thereby forming said air bearing means between said housing means and the sheet material.

12. A method for determining the quality of a travelling sheet material, comprising the steps of directing light from a surface of the travelling sheet material only through a relatively narrow air gap into a series of apertures of different sizes arranged in progressively larger sizes in the direction of sheet travel, converting the thus-directed light into electrical signals while detecting when said signals depart from predetermined values for indicating when flaws of a given size are present at the sheet material, regularly traversing said apertures cyclically first in one direction then in an opposite direction across the travelling sheet, and converting the detected departures of said signals from said given values into an indication of the quality of the sheet material.

13. The method of claim 12 and wherein a warning is automatically given when the indicated quality is poorer than a predetermined lowest quality limit.

* * * * *